(12) United States Patent
Sato et al.

(10) Patent No.: US 9,207,182 B2
(45) Date of Patent: Dec. 8, 2015

(54) ANALYSIS METHOD OF VIBRATIONAL SPECTRA (75) Inventors: Akira Sato, Tokyo (JP); Takeshi Watanabe, Tokyo (JP); Shinichi Takimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 279 days.

(21) Appl. No.: 13/032,145

(22) Filed: Feb. 22, 2011

(65) Prior Publication Data

US 2012/0065899 A1  Mar. 15, 2012

Related U.S. Application Data (60) Provisional application No. 61/308,040, filed on Feb. 25, 2010.

(30) Foreign Application Priority Data

Mar. 18, 2010 (JP) ................................ 2010-062550

(51) Int. Cl.
G01N 21/65 (2006.01)
(52) U.S. Cl.
CPC .......... *G01N 21/65* (2013.01); *G01N 2021/653* (2013.01)
(58) Field of Classification Search
CPC ............ G01N 21/65; G01N 2021/655; G01N 2021/653; H01J 49/0036
USPC .......................................................... 702/23
See application file for complete search history.

(56) References Cited

U.S. PATENT DOCUMENTS

| 8,013,991 B2 * | 9/2011 | Maier et al. ............... 356/301 |
| 2006/0183236 A1 * | 8/2006 | Berlin et al. ............... 436/94 |
| 2009/0001262 A1 * | 1/2009 | Visser et al. ............... 250/282 |

FOREIGN PATENT DOCUMENTS

| JP | 2003-535330 A | 11/2003 |
| WO | 01/92859 A1 | 12/2001 |

OTHER PUBLICATIONS

Romeo, M.J., et al. "Infrared and Raman Microspectroscopic Studies of Individual Human Cells", Vibrational Spectroscopy for Medical Diagnosis 2008, John Wiley & Sons, pp. 27-63.
Karpushkin, E., et al. "New System for Computer-aided Infrared and Raman Spectrum Interpretation", Chemometrics and Intelligent Laboratory Systems, Aug. 15, 2007, vol. 88, No. 1, pp. 107-117.

* cited by examiner

*Primary Examiner* — Eliseo Ramos Feliciano
*Assistant Examiner* — Terence Stifter, Jr.
(74) *Attorney, Agent, or Firm* — Scully, Scott, Murphy & Presser, P.C.

(57) ABSTRACT

A plurality of Raman spectral datasets of an unknown sample acquired under the same measurement conditions is selected in a plurality of Raman spectral data items having different spectral profiles acquired by setting different measurement conditions in a plurality of unknown mixed samples, a spectrum acquired under the same measurement conditions as those of the Raman spectral dataset of the unknown sample is selected in the spectra of the benchmark molecule to be classified, a PCA loading is calculated from the Raman spectral dataset of the unknown sample, the correlation between the calculated PCA loading and the selected spectrum of the benchmark molecule to be classified is calculated, and the PCA loading having a highest correlation with the spectrum of the benchmark molecule to be classified is determined in the PCA loadings calculated from a plurality of Raman spectral datasets of the unknown sample having different measurement conditions.

1 Claim, 8 Drawing Sheets

ANALYSIS METHOD OF VIBRATIONAL SPECTRA

CROSS REFERENCE TO RELATED APPLICATIONS

This application claims the benefit of U.S. Provisional Application No. 61/308,040, filed Feb. 25, 2010, which is hereby incorporated by reference herein in its entirety. This application claims the benefit of Japanese Patent Application No. 2010-062550, which is hereby incorporated by reference herein in its entirety.

TECHNICAL FIELD

The present invention relates to a vibrational spectrum analysis method.

BACKGROUND ART

In the past, in order to perform classification of the chemical states of biological samples including many types of molecules, or concentration estimation (calibration) of components included in the biological samples, a method of a multivariate analysis (chemometrics) has been adopted in which vibrational spectra (Raman spectra or infrared absorption spectra) of a biological sample are acquired, and intensity information of the entire frequency region in the acquired vibrational spectra is treated as a variate (see, for example, U.S. Pat. No. 6,341,257).

According to such a method of chemometrics, vibrational bands (Raman bands or infrared absorption bands) given by each component included in the biological sample are superimposed on the spectrum. Therefore, as long as a frequency domain having a low correlation between spectral profiles given by each component exists in the acquired vibrational spectrum even when the vibrational spectrum of the sample exhibits an intensity pattern (spectral profile) of a complex spectrum, it is possible to perform calibration or classification of the chemical states of the biological sample on the basis of information of the vibrational spectrum.

Specifically, since nucleic acid and protein included in the biological sample are significantly different in chemical composition or molecular structure, the correlation of the spectral profile between the vibrational spectra is low. Alternatively, in a plurality of types of proteins included in the biological sample, when there is a significant difference in the frequency of appearance of a specific amino-acid side chain or in the steric structure (secondary structure or tertially structure), the correlation of the spectral profile between the vibrational spectra of these proteins also becomes low.

In the biological sample to be analyzed, when the types or the relative amounts of such a component (molecule) having a low correlation of the spectral profile fluctuates for each sample, it is possible to classify the states of the sample from distribution of the score plot (PCA score plot) of a principle component by executing principle component analysis (Principle Component Analysis, hereinafter, referred to as the PCA) with respect to the vibrational spectra. In addition, it is also possible to estimate the concentration of the component included in the sample by creating a calibration curve on the basis of the vibrational spectra of a reference sample.

In chemometrics, the calibration curve is created by calculating a calibration matrix, and as an algorithm for calculating the calibration matrix, a CLS (Classical Least Squares Fitting) method and an ILS (Inverse Least Squares Fitting) method in which the result of the PCA is not used, and a PCR (Principle Component Regression) method and a PLS (Partial Least Squares Fitting) method which are based on the PCA result (PCA score value) are adopted.

CITATION LIST

Patent Literature

{PTL 1}
Specification of U.S. Pat. No. 6,341,257

Non Patent Literature

{NPL 1}
Max Diem, Peter R Griffiths and John M Chalmers, "Vibrational spectroscopy for medical diagnosis" (2008, John Wiley & Sons)

SUMMARY OF INVENTION

Technical Problem

However, actually, when the biological sample is a mixed sample composed of a plurality of biomolecules such as a cell, a tissue or a body fluid, many types of molecules which are similar in chemical composition and not extremely different in steric structure, as represented by protein, are included in the sample. Therefore, a component having a low correlation of the spectral profile between the vibrational spectra, like nucleic acid and protein, is also included in the sample, but a component having a high correlation of the spectral profile between the vibrational spectra is generally included in the sample as well. As described above, as an example in which the component having a high correlation between the spectra is included, many types of proteins are included in the sample, and it is considered that there is rough similarity in the amino-acid side chains and the secondary structure of these proteins, or that nucleic acid chemically modified by an epigenetic action or the same type of protein chemically modified after being translated is present.

In chemometrics, by using an observation channel of the spectrum (observation point on a frequency axis in the spectrum) as a coordinate axis, the vibrational spectrum of the sample is represented as one point in the multidimensional space (multivariate space) in which the spectral intensity in each observation channel is set to a variate in the coordinate axis. Alternatively, with the same meaning, in the multivariate space, the vibrational spectrum is represented as a multidimensional vector attracted from the origin to one point in the space. Thus, in the multivariate space, the vibrational spectra of a plurality of samples are represented as a plurality of dispersion points, that is, a point set (point group) having a certain distribution, or are represented as a multidimensional vector group from the origin to a plurality of dispersion points. The PCA is a method of resetting the coordinate axises (PCA loadings) in the multivariate space so as to quantitatively take features of the point group distribution of the vibrational spectrum in such a multivariate space, and classifying the samples on the basis of position information (PCA score) of the vibrational spectrum in the space expanded by the PCA loadings.

In the state, as mentioned above, where the components having a high correlation of the spectral profile between the vibrational spectra exist in the biological sample, and the types or the relative amounts thereof fluctuates for each sample, when the vibrational spectrum of the sample is made to correspond to points in the multivariate space, the spectrum is concentrated on the same region in the multivariate space, and the spatial dispersion becomes small. Therefore, in the PCA for evaluating the spread of the spatial dispersion of the spectrum, the classification itself is impossible due to the lack of the classification accuracy of the sample spectrum. In addition, even in the object of calibration, since the PCR method and the PLS method are method (of calculating a calibration matrix from the PCA score) based on the PCA, and the PCA score of the spectrum of the sample is invariable irrespective of the relative concentration of the components, it is impossible to separate the components and perform the calibration thereof. Similarly, in the CLS adopted in the object of calibration, the correlation of the spectra (CLS loadings) of each component of the sample which is required at the time of calculating the calibration matrix becomes high (collinearity in spectrum), the calibration accuracy is deteriorated. As a result, it is not possible to perform the analysis such as classification of the unknown mixed sample or calibration of the components with a high degree of accuracy.

The invention provides analysis methods of vibrational spectra which are capable of performing classification of the sample or calibration of the components with a high degree of accuracy even when the types or the relative amounts of the components having a high correlation of the spectral profiles fluctuates for each sample.

Solution to Problem

According to a first aspect of the invention, there is provided a vibrational spectrum analysis method including: a dataset selection step of selecting a Raman spectral dataset of an unknown sample including Raman spectral data of a plurality of unknown mixed samples acquired under the same measurement conditions, in a plurality of Raman spectral data items having different spectral profiles acquired with respect to the plurality of unknown mixed samples including a plurality of unknown components at an unknown mixture ratio by setting different measurement conditions in each of the unknown mixed samples; a spectrum selection step of selecting a spectrum acquired under the same measurement conditions as those of the Raman spectral dataset of the unknown sample selected in the dataset selection step, in spectra of a benchmark molecule to be classified which is set as a desired component when classification of a chemical state of the unknown sample is executed in accordance with which ratio of the desired component is included in the unknown mixed sample; a calculation step of calculating PCA loadings by executing a PCA with respect to the Raman spectral dataset of the unknown sample selected in the dataset selection step; a correlation calculation step of calculating a correlation of a spectrum waveform between the PCA loadings calculated in the calculation step and the spectrum of the benchmark molecule to be classified selected in the spectrum selection step; and a determination step of determining a PCA loading which has the highest correlation of a spectral waveform with the spectrum of the benchmark molecule to be classified, in PCA loadings calculated from a plurality of Raman spectral datasets of the unknown sample having different measurement conditions.

According to the above-mentioned first aspect, the PCA loadings are calculated for each Raman spectral dataset of the unknown sample selected from among a plurality of Raman spectral data items having different spectral profiles which are acquired by setting different measurement conditions in the unknown mixed samples, and a PCA loading having the highest correlation with the spectrum of the benchmark molecule to be classified is determined in all calculated PCA loadings. Therefore, it is possible to perform rotation and multiplication operations with respect to a spectrum group of the unknown mixed sample which is represented as a point group degenerated in the multivariate space, that is, a vector group of the unknown mixed sample degenerated in the multivariate space to thereby generate the spatial dispersion in the spectrum group of the unknown mixed sample in the multivariate space, and to maximize contribution of the spectrum dispersion of the benchmark molecule to be classified to the above-mentioned dispersion. As a result, it is possible to extract loading information of a principle component having a high correlation with the spectrum of the benchmark molecule to be classified which is intended to be classified, and to classify the unknown mixed sample with a high degree of accuracy on the basis of the difference of the concentration of the benchmark molecule to be classified using this principle component loading.

In the above-mentioned first aspect, it is preferable that the vibrational spectrum analysis method includes a classification step of classifying the sample by plotting a PCA score with respect to the PCA loadings determined in the determination step.

In this manner, it is possible to easily classify the unknown mixed samples with a high degree of accuracy by plotting the PCA score using the PCA loadings, which is loading information of the principle component, having a high correlation with the spectrum of the benchmark molecule to be classified which is intended to be classified.

According to a second aspect of the invention, there is provided a vibrational spectrum analysis method including: a reference sample dataset selection step of selecting a Raman spectral dataset of a reference sample including Raman spectral data of a plurality of reference mixed samples acquired under the same measurement conditions, in a plurality of Raman spectral data items having different spectral profiles acquired with respect to the plurality of reference mixed samples including a plurality of known components at a known mixture ratio by setting different measurement conditions in each of the reference mixed samples; a calculation step of calculating a plurality of CLS loadings from the Raman spectral dataset of a reference sample selected in the reference sample dataset selection step; a correlation calculation step of calculating a correlation between the plurality of CLS loadings calculated in the calculation step; a determination step of determining a dataset for calibration which has the lowest correlation between the CLS loadings calculated in the correlation calculation step, in a plurality of Raman spectral datasets of a reference sample having different measurement conditions; a calibration matrix calculation step of calculating a calibration matrix using the dataset for calibration determined in the determination step; an unknown sample dataset selection step of selecting a Raman spectral dataset of an unknown sample including Raman spectral data of one or more unknown mixed samples, including a plurality of unknown components at an unknown mixture ratio, which are measured under the same measurement conditions as those of the dataset for calibration determined in the determination step; and a calibration step of multiplying the Raman spectral dataset of the unknown sample selected in the unknown sample dataset selection step by the calibration matrix calculated in the matrix calculation step.

According to the above-mentioned second aspect, the a plurality of CLS loadings is calculated for each Raman spectral dataset of the reference sample selected from a plurality of Raman spectral data items having different spectral profiles which are acquired by setting different measurement conditions in the reference mixed samples, and the dataset for calibration having the lowest correlation between the calculated CLS loadings is determined. The calibration matrix calculated from the determined dataset for calibration is multiplied by the Raman spectral dataset of the unknown sample, and rotation and multiplication operations are performed with respect to a component spectrum group in the unknown mixed sample which is represented as a point group degenerated in the multivariate space, that is, a component vector group in the unknown mixed sample degenerate in the multivariate space, whereby it is possible to calibrate the amount of each of the components included in the unknown mixed sample with a high degree of accuracy by lowering the correlation of each spectrum of the component of the unknown mixed sample.

According to a third aspect of the invention, there is provided a vibrational spectrum analysis method including: a reference sample dataset selection step of selecting a Raman spectral dataset of a reference sample including Raman spectral data of a plurality of reference mixed samples acquired under the same measurement conditions, in a plurality of Raman spectral data items having different spectral profiles acquired with respect to the plurality of reference mixed samples including a plurality of known components at a known mixture ratio by setting different measurement conditions in each of the reference mixed samples; a spectrum selection step of selecting a spectrum acquired under the same measurement conditions as those of the Raman spectral dataset of a reference sample selected in the reference sample dataset selection step, in spectra of a molecule to be calibrated which is a component intended to be calibrated; a calculation step of calculating PCA loadings from the Raman spectral dataset of a reference sample selected in the reference sample dataset selection step; a correlation calculation step of calculating a correlation between the PCA loadings calculated in the calculation step and the spectrum of the molecule to be calibrated which is selected in the spectrum selection step; a determination step of determining a PCA loading which has the highest correlation with the spectrum of the molecule to be calibrated, in PCA loadings calculated from a plurality of Raman spectral datasets of a reference sample having different measurement conditions; a calibration matrix calculation step of calculating a calibration matrix using the Raman spectral dataset of a reference sample determined in the determination step; an unknown sample dataset selection step of selecting a Raman spectral dataset of an unknown sample including Raman spectral data of a plurality of unknown mixed samples, including a plurality of unknown components at an unknown mixture ratio, which are measured under the same measurement conditions as those of the Raman spectral dataset of a reference sample determined in the determination step; and a calibration step of multiplying the Raman spectral dataset of an unknown sample selected in the unknown sample dataset selection step by the calibration matrix calculated in the matrix calculation step.

According to the above-mentioned third aspect, the PCA loadings are calculated for each Raman spectral dataset of the reference sample selected from among a plurality of Raman spectral data items having different spectral profiles which are acquired by setting different measurement conditions in the reference mixed samples, and the calibration matrix is calculated using the Raman spectral dataset of the reference sample having a highest correlation with the spectrum of the molecule to be calibrated acquired under the same measurement conditions as those of the selected Raman spectral dataset of the reference sample. The calculated calibration matrix is multiplied by the Raman spectral dataset of the unknown sample, and rotation and multiplication operations are performed with respect to a component spectrum group which is represented as a point group degenerated in the multivariate space, that is, a vector group of the spectrum of the component degenerated in the multivariate space, it is possible to maximize contribution of the spectrum dispersion of the molecule to be calibrated to the dispersion of the spectrum of the unknown mixed sample. As a result, it is possible to extract loading information of a principle component having a high correlation with the spectrum of the molecule to be calibrated which is intended to be calibrated, and to calibrate each of the components of the unknown mixed sample with a high degree of accuracy using this principle component loading.

According to a fourth aspect of the invention, there is provided a vibrational spectrum analysis method including: an unknown sample dataset selection step of selecting a Raman spectral dataset of an unknown sample including Raman spectral data of a plurality of unknown mixed samples acquired under the same measurement conditions, in a plurality of Raman spectral data items having different spectral profiles acquired in a first frequency domain with respect to the plurality of unknown mixed samples including a plurality of unknown components at an unknown mixture ratio by setting different measurement conditions in each of the unknown mixed samples; an unknown sample data combination step of combining the Raman spectral data of each of the unknown mixed samples selected in the dataset selection step and external Raman spectral data of an unknown sample acquired in a frequency domain different from the first frequency domain with respect to each of the unknown mixed samples, to generate an expanded Raman spectral dataset of an unknown sample; a benchmark molecule spectrum selection step of selecting a spectrum acquired under the same measurement conditions as those of the Raman spectral dataset of an unknown sample selected in the dataset selection step, in a plurality of Raman spectral data items having different spectral profiles acquired in a second frequency domain with respect to a benchmark molecule to be classified which is a component intended to be classified; a benchmark molecular data combination step of combining the spectrum selected in the benchmark molecule spectrum selection step and an external Raman spectrum of a benchmark molecule acquired in a frequency domain different from the second frequency domain with respect to the benchmark molecule to be classified, to generate expanded Raman spectral data of a benchmark molecule; a calculation step of calculating PCA loadings from the expanded Raman spectral dataset of an unknown sample generated in the unknown sample data combination step; a correlation calculation step of calculating a correlation between the PCA loadings calculated in the calculation step and the expanded Raman spectral data of a benchmark molecule generated in the benchmark molecular data combination step; and a determination step of determining a PCA loading which has the highest correlation with the expanded Raman spectral data of a benchmark molecule, in PCA loadings calculated from a plurality of expanded Raman spectral datasets of an unknown sample having different measurement conditions.

According to the above-mentioned fourth aspect, the expanded Raman spectral dataset of the unknown sample and the expanded Raman spectral data of the benchmark molecule are generated by combining the external Raman spectral data of the unknown sample and the external Raman spectrum of the benchmark molecule, which are acquired in a different frequency domain, with the Raman spectral dataset of the unknown sample and the spectrum of the benchmark molecule to be classified. Therefore, the number of dimensions of the multivariate space is expanded, whereby it is possible to generate the dispersion in a vector group of the spectra of the unknown sample and the benchmark molecule to be classified, which are degenerated in the multivariate space, before the number of dimensions is expanded, and to increase contribution of the spectrum dispersion of the benchmark molecule to be classified to the dispersion of the spectrum of the unknown mixed sample. As a result, it is possible to extract loading information of a principle component having a high correlation with the spectrum of the benchmark molecule to be classified which is intended to be classified, and to classify the unknown mixed sample with a high degree of accuracy on the basis of the difference of the concentration of the benchmark molecule to be classified using this principle component loading.

In the above-mentioned fourth aspect, it is preferable to include a classification step of classifying the unknown mixed samples by plotting a PCA score with respect to the PCA loadings determined in the determination step.

In this manner, it is possible to easily classify the unknown mixed samples with a high degree of accuracy by plotting the PCA score using the PCA loadings, which are loading information of the principle component, having a high correlation with the spectrum of the benchmark molecule to be classified which is intended to be classified.

DESCRIPTION OF EMBODIMENTS

A vibrational spectrum analysis method according to a first embodiment of the invention will be described with reference to the drawings. The vibrational spectrum analysis method according to the embodiment is a method of classifying spectra of a plurality of unknown mixed samples to be analyzed by the PCA on the basis of spectral information of a desired benchmark molecule to be classified.

Here, the unknown mixed sample means a sample which is analyzed on the basis of the result of acquisition of vibrational spectral data (which may be Raman spectral data or infrared absorption spectral data) and the chemometrics analysis regarding the spectral data, and includes a plurality of unknown components at an unknown mixture ratio. For example, mixed materials including a plurality of types of molecules (small molecules and the like within a biological body such as nucleic acid, protein A, protein B, . . . , lipid, saccharide, other information transfer molecules or coenzymes) like a cell, a tissue, or a body fluid are envisioned. One or more unknown mixed samples may be prepared.

Here, the benchmark molecule to be classified means a molecule becoming the criterion for classification at the time of classifying the unknown mixed sample by the PCA, and for example, it is envisioned to be a specific protein molecule, or a specific lipid or saccharide molecule. As the benchmark molecule to be classified, one kind of molecule may be prepared, or two kinds of molecules may be prepared.

Figure 1:
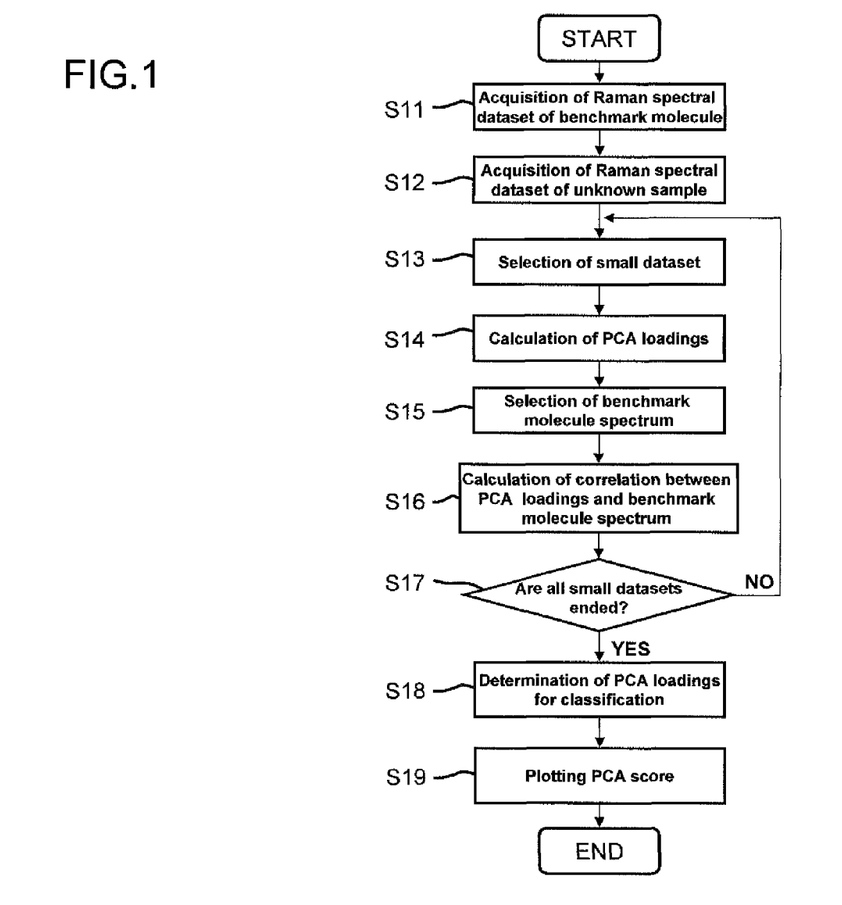
FIG. 1 is a flow diagram illustrating a vibrational spectrum analysis method according to a first embodiment of the invention.
Figure 2:
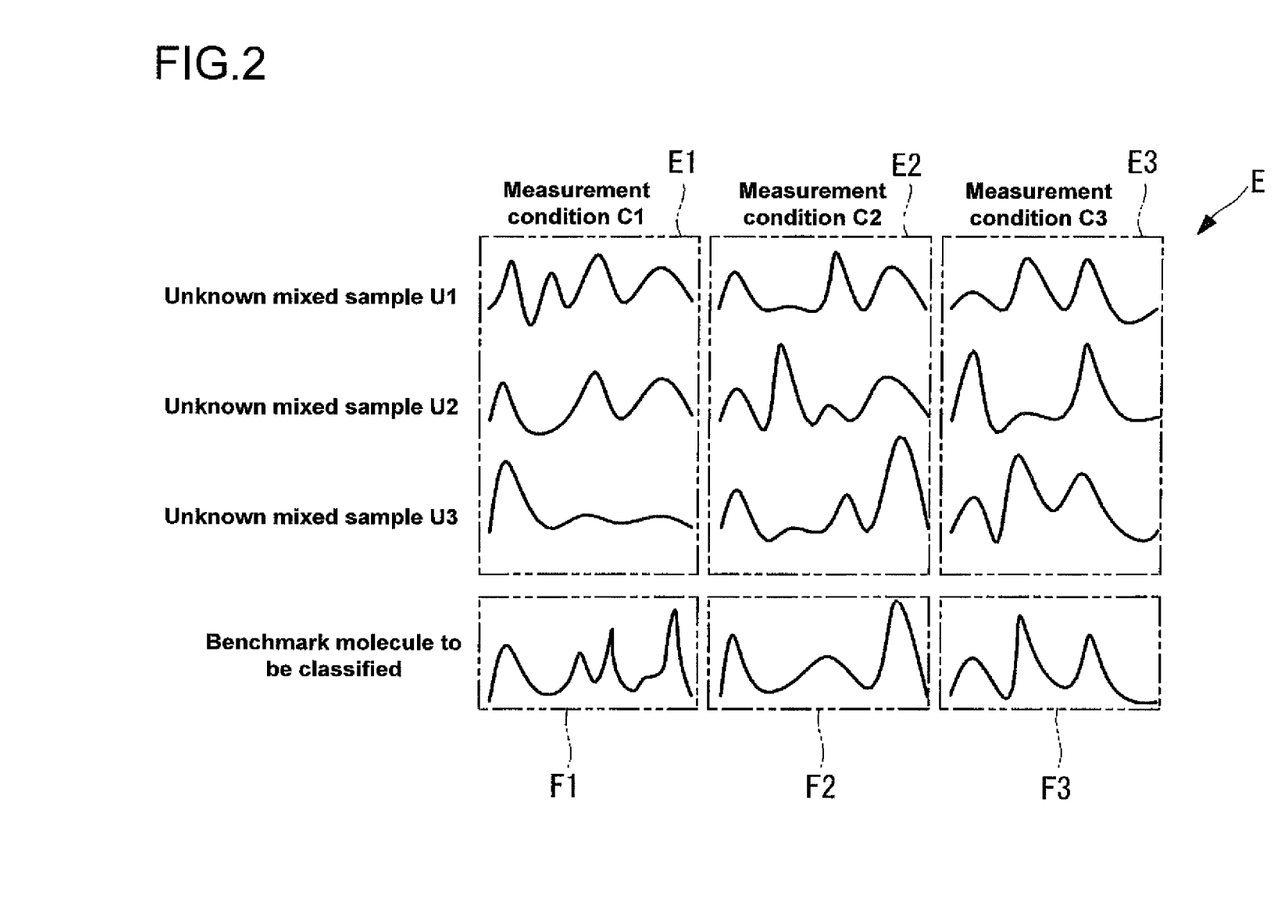
FIG. 2 is a diagram illustrating an example of a Raman spectral dataset of an unknown sample including Raman spectral data of a plurality of unknown mixed samples used in the vibrational spectrum analysis method of FIG. 1 and benchmark molecule Raman spectral data of a benchmark molecule to be classified.

In the vibrational spectrum analysis method according to the embodiment, as shown in FIG. 1, a Raman spectral dataset of an unknown mixed sample and a benchmark molecule to be classified are acquired. Here, as shown in FIG. 2, a plurality of different measurement conditions, that is, C1 to C3 of FIG. 2 is set with respect to a plurality of unknown mixed samples and a benchmark molecule to be classified and Raman spectra having different spectral profiles are acquired. Although three different measurement conditions of C1 to C3 are shown in FIG. 2, the number of these measurement conditions is arbitrary insofar as the number is plural. Next, in what follows, a method of acquiring Raman spectra having different spectral profiles will be described in detail.

In a nonlinear Raman scattering method, it is possible to acquire a plurality of Raman spectra having different spectral profiles in the same frequency domain of the same sample by changing the light irradiation conditions of the sample or the detection conditions thereof at the time of acquiring the Raman spectra. For example, when a relative angle is set with respect to polarization of two-color laser light for Raman scattering excitation with which the sample is irradiated, or a relative angle is set even with respect to polarization of laser light for probing Raman scattering, the orientation of polarization of signal light is dispersed in accordance with the degree of depolarization of a Raman band of each component (molecular species) included in the sample. In this case, it is possible to acquire a plurality of Raman spectra having different spectral profiles caused by the difference between the degrees of depolarization of the Raman band given by each component included in the sample by measuring a signal under the different polarization selection conditions for the signal light such as a change of the angle of the transmission axis of an analyzer, that is, by measuring the signal under different measurement conditions of the signal. Alternatively, the relative polarization angle of the laser light with which the sample is irradiated may be changed. This allows at least two different measurement conditions to be selected.

Such a nonlinear Raman scattering method includes an SRS (stimulated Raman scattering) method, a CARS (coherent anti-Stokes Raman scattering) method, a CSRS (coherent Stokes Raman scattering) method, an ISRS (impulsive stimulated Raman scattering) method, RIKES (Raman induced Kerr effect spectroscopy), or vibrational spectroscopy based on a four-wave-mixing process as a form including these detection methods. In addition, even in a linear Raman scattering method (spontaneous Raman scattering method), when the polarization of the laser light for Raman scattering excitation is set, and then the measurement is performed by changing the angle of the transmission axis of the analyzer to set different polarization selection conditions of the signal, a plurality of Raman spectra having different spectral profiles can be acquired.

Alternatively, the method of acquiring the Raman spectra having different spectral profiles may be the following method. In the above-mentioned nonlinear Raman scattering method, when the sample is irradiated with the two-color laser light for Raman scattering excitation by adding time delays to probe laser light, the band intensity of the Raman spectrum of the signal light in each time delay is changed depending on the vibrational phase relaxation time of a vibrational mode of the component (molecule) included in the sample (time-resolved CARS method). In addition, even when the two-color laser light for Raman scattering excitation is multiple-pulsed, and then the repetition frequency of the multiple-pulse is scanned, the band intensity of the Raman spectrum of the signal light is similarly changed depending on the vibrational phase relaxation time of a vibrational mode (multi-pulse impulsive stimulated Raman scattering method). Therefore, even when the signal is measured at different timings of the laser light with which the sample is irradiated, a plurality of Raman spectra having different spectral profiles can be acquired.

Alternatively, the spectral profiles may be made to be different, using at least two different types of spectroscopic methods, by adding the measurement method different from the nonlinear Raman scattering method in addition to acquisition of the spectra having different spectral profiles by setting different measurement conditions such as the polarization or the irradiation timing of irradiation laser light and polarization selection of the signal light in the nonlinear Raman scattering method. An example of the different measurement method added in this case includes a spontaneous Raman scattering method (electronically nonresonant Raman scattering, electronically resonant Raman scattering).

Alternatively, using at least two different nonlinear Raman scattering methods, the spectra having different spectral profiles may be acquired by setting different measurement conditions such as the polarization or the irradiation timing of irradiation laser light and polarization selection of the signal light.

As shown in FIG. 1, first, in the benchmark molecule to be classified, a Raman spectral dataset of the benchmark molecule including Raman spectral data having different spectral profiles is acquired by switching the measurement conditions C1 to C3 to acquire the Raman spectra (step S11). In FIG. 2, the case is shown where Raman spectral datasets F1 to F3 of the benchmark molecule are acquired with respect to one kind of a benchmark molecule P1 to be classified.

Next, a Raman spectral dataset E of an unknown sample including a plurality of Raman spectral data items of unknown mixed samples U1 to U3 is acquired (step S12).

As shown in FIG. 2, the Raman spectra having different spectral profiles are acquired with respect to the unknown mixed samples U1 to U3 by setting different measurement conditions C1 to C3 for each of a plurality of unknown mixed samples U1 to U3. At the time of acquisition of the above-mentioned Raman spectra, the measurement is performed with respect to each of the unknown mixed samples U1 to U3. Thereby, a plurality of Raman spectral data items acquired by setting different measurement conditions C1 to C3 is obtained for each of the unknown mixed samples U1 to U3. That is, the Raman spectral dataset E of the unknown sample including the Raman spectral data of a number corresponding to the number of the product of the number of the measurement conditions and the number of the unknown mixed samples is acquired.

Next, any of small datasets E1 to E3 is selected from the Raman spectral dataset E of the unknown sample (step S13). The small datasets E1 to E3 are indicative of a set of the Raman spectral data acquired under the same measurement conditions in the Raman spectral dataset E of the unknown sample. For example, in the example shown in FIG. 2, the Raman spectral data having different spectral profiles are acquired by acquiring the Raman spectra, respectively, under three kinds of the measurement conditions C1 to C3 with respect to each of the unknown mixed samples U1 to U3, and at first, the small dataset E1 including three Raman spectral data items in a vertical column of the measurement conditions C1 is selected from them.

Next, a PCA loading is calculated using the selected small dataset E1 (step S14). The PCA loading can be regarded as a vector directed to the direction of the coordinate axis which is reset in the multivariate space so as to maximally take spatial dispersion of the Raman spectra of unknown mixed samples U1 to U3 plotted in the multivariate space expanded by the measurement channel axis, whereby a Raman spectrum-like waveform is formed.

The calculation of the PCA loading is performed by a well-known method, and one or more PCA loadings are calculated with respect to the small dataset E1.

The Raman spectral data F1 measured under the same measurement conditions C1 as those of the small dataset E1 which is acquired in step S11 and selected in step S13 are selected from among the Raman spectral datasets F1 to F3 of the benchmark molecule (step S15).

The correlation between the selected Raman spectral data F1 of the benchmark molecule P1 to be classified and the PCA loading of the small dataset E1 calculated in step S14 is calculated (step S16). The correlation between the Raman spectral data and the PCA loading can be estimated as, for example, the Euclidean distance between two points on the multivariate space, corresponding to the Raman spectral data and the PCA loading, which is specified in the multivariate space having a coordinate axis for each observation channel of the spectrum, or the Mahalanobis distance. Alternatively, the correlation may be estimated as a size of the coefficient of correlation between the Raman spectral data and the PCA loading which is used in the HCA (hierarchy clustering analysis). Here, when the correlation between the PCA loading which is a loading of the principle component included in the unknown mixed samples U1 to U3 and the Raman spectral data F1 of the benchmark molecule P1 to be classified is high, it is possible to select the principle component axis capable of satisfactorily taking concentration fluctuation of the benchmark molecule P1 to be classified within the unknown mixed samples U1 to U3.

Consequently, these steps S13 to S16 are repeated with respect to the small datasets E2 and E3 (step S17), so that the correlations between the PCA loadings of the small dataset of the unknown mixed samples U1 to U3 of all measurement conditions C1 to C3 and the Raman spectral data F1 to F3 of the benchmark molecule P1 to be classified are calculated, and the calculated correlations are compared with each other to determine the PCA loading having a highest correlation as a PCA loading for classification (step S18). Using the determined PCA loading for classification, the PCA score is plotted for each of the unknown mixed samples U1 to U3 (step S19). Thereby, the unknown mixed samples U1 to U3 are classified with respect to the benchmark molecule P1 to be classified.

In this manner, according to the vibrational spectrum analysis method of the embodiment, since the classification is performed on the basis of the PCA loading capable of most satisfactorily grasping the concentration fluctuation of the benchmark molecule P1 to be classified for each of the unknown mixed samples U1 to U3, there is an advantage that, by performing rotation and multiplication operations on the spectra of which the direction is degenerated in the multivariate space, it is possible to maximize contribution of the spectrum dispersion of the specific benchmark molecule P1 to be classified to dispersion of the spectra of each of the unknown mixed samples U1 to U3, and to perform the classification in the spectra of the unknown mixed samples U1 to U3 with a high degree of accuracy in accordance with the size of the contribution of the benchmark molecule P1 to be classified.

Meanwhile, in the embodiment, the Raman spectral datasets F1 to F3 of the benchmark molecule P1 to be classified are acquired, and then the Raman spectral dataset E of the unknown mixed samples U1 to U3 is acquired, but instead, the order may be reversed. In addition, the order of calculation step S14 of the PCA loading and selection step S15 of the spectrum of the benchmark molecule may be changed.

The vibrational spectrum analysis method according to a second embodiment of the invention will be described below with reference to the drawings. The vibrational spectrum analysis method according to the embodiment is a method of performing a CLS calibration of components of the unknown mixed sample to be analyzed.

Figure 3:
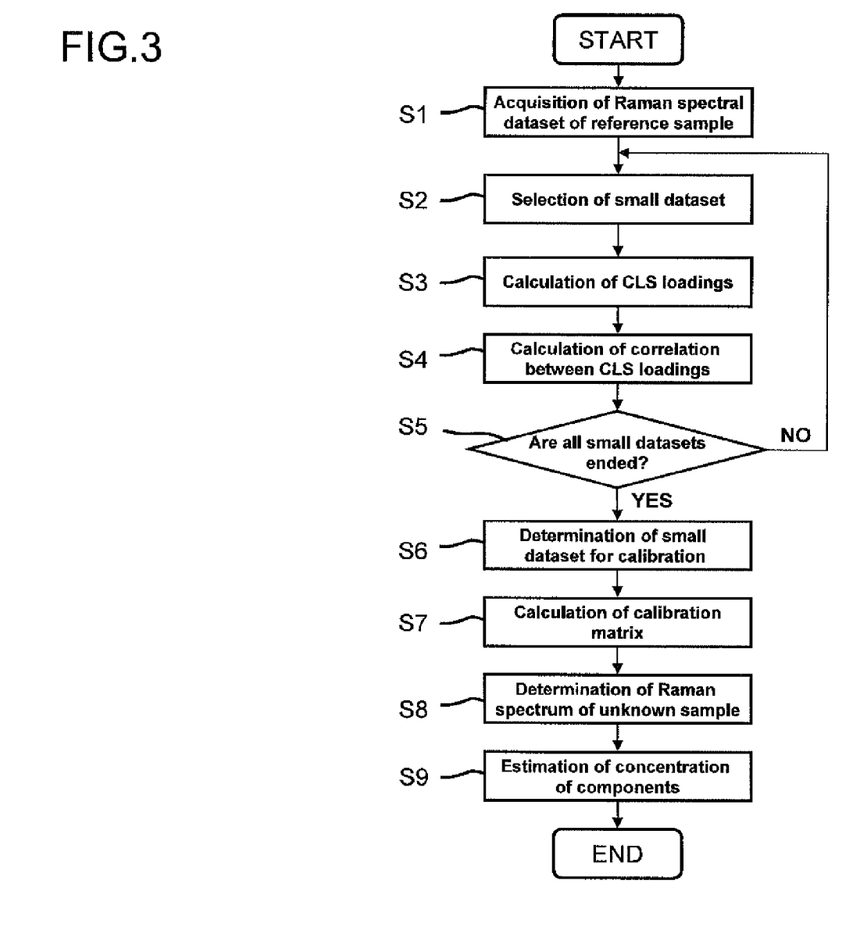
FIG. 3 is a flow diagram illustrating the vibrational spectrum analysis method according to a second embodiment of the invention.

In the vibrational spectrum analysis method according to the embodiment, as shown in FIG. 3, first, a Raman spectral dataset of a reference sample including a plurality of Raman spectral data items of a reference mixed sample for calculating a calibration matrix is acquired (step S1).

Here, the reference mixed sample is a sample for creating the calibration matrix used in the time of calibrating the concentration of a molecule to be calibrated included in the unknown mixed sample, and is a material created by changing the mixture ratio of a plurality of known components (for example, nucleic acid, protein A, protein B, lipid, saccharide, a small molecule within the biological body, and the like) expected to be included in the unknown mixed sample and performing mixing. The reference mixed sample is, for example, a mixed solution, and a plurality of reference mixed samples having known different mixture ratios is prepared.

Figure 4:
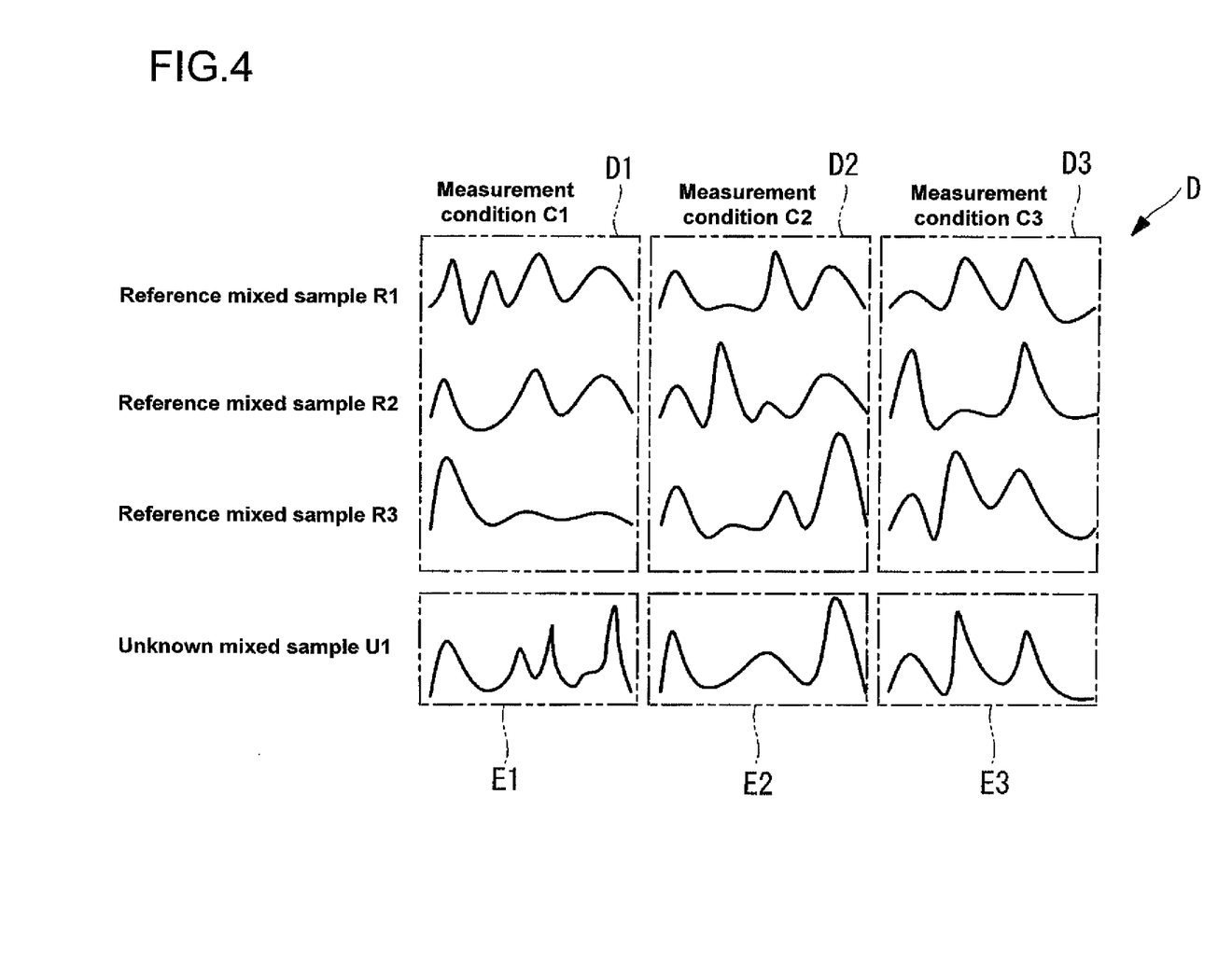
FIG. 4 is a diagram illustrating an example of a Raman spectral dataset of a reference sample including Raman spectral data of a plurality of reference mixed samples used in the vibrational spectrum analysis method of FIG. 3 and unknown sample Raman spectral data of an unknown mixed sample.

As shown in FIG. 4, the Raman spectra having different spectral profiles are acquired with respect to the reference mixed samples by setting different measurement conditions for each of a plurality of reference mixed samples R1 to R3.

Here, a method of acquiring the Raman spectra having different spectral profiles is a method based on the spectrum acquisition method in the first embodiment mentioned above.

When the Raman spectra of each of the reference mixed samples R1 to R3 are acquired, the measurement is performed with respect to each of the reference mixed samples R1 to R3 by setting a plurality of measurement conditions. Thereby, a plurality of Raman spectral data items acquired by setting different measurement conditions is obtained for each of the reference mixed samples R1 to R3. That is, a Raman spectral dataset D of the reference sample including the Raman spectral data of a number corresponding to the number of the product of the number of the measurement conditions and the number of the reference mixed samples is acquired.

Next, any of small datasets D1, D2, and D3 is selected from the Raman spectral dataset D of the reference sample (step S2). The small datasets D1 to D3 are indicative of a set of Raman spectral data acquired under the same measurement conditions in the Raman spectral dataset D of the reference sample. For example, in the example shown in FIG. 4, the Raman spectral data having different spectral profiles are acquired by acquiring the Raman spectra, respectively, under three kinds of measurement conditions C1 to C3 with respect to each of the reference mixed samples R1 to R3, and at first, the small dataset D1 including three Raman spectral data in a vertical column of the measurement conditions C1 is selected from them.

Next, the CLS loading is calculated using the selected small dataset D1 (step S3).

The calculation of the CLS loading is performed by a heretofore known method, and a plurality of CLS loadings is calculated with respect to the small dataset D1.

The correlation of the spectrum waveforms is calculated between a plurality of CLS loadings of the small dataset D1 calculated in this manner (step S4). The correlation between the CLS loadings can be estimated as, for example, the Euclidean distance between two points on the multivariate space, corresponding to the two CLS loading, which is specified in the multivariate space having a coordinate axis for each observation channel of the spectrum, or the Mahalanobis distance. That is, the correlation between the CLS loadings which are spectrum-like waveforms equivalent to the spectrum of the individual components included in the reference mixed samples R1 to R3 is high, collinearity exists in the calibration matrix calculated from this, which leads to deterioration of the detection accuracy.

Consequently, these steps S2 to S4 are repeated similarly with respect to the small datasets D2 and D3 (step S5), so that the correlation between the CLS loadings is calculated with respect to the small datasets D1 to D3 of all measurement conditions C1 to C3, and the high and low levels of the calculated correlation are compared with each other to determine the small dataset (for example, small dataset D1) having the lowest correlation between the CLS loadings as a small dataset for calibration (step S6). The calibration matrix is calculated using the determined small dataset for calibration (step S7).

In addition, when the small dataset for calibration is determined, the Raman spectral data E1 of the unknown sample is determined which is acquired by performing the measurement with respect to the unknown mixed sample U1 under the same measurement conditions C1 as the measurement conditions C1 at the time of acquiring the small dataset for calibration (step S8). It is possible to perform the calibration of the components within the unknown mixed sample by multiplying the determined Raman spectral data E1 of the unknown sample by the calculated calibration matrix (step S9).

According to the vibrational spectrum analysis method of the embodiment having such a configuration, since the Raman spectrum dataset D1 having the lowest correlation between the CLS loadings calculated from the small dataset for calibration is selected as the small dataset for calibration for calculating the calibration matrix, there is an advantage that the Raman spectra of the sample having different spectral profiles are acquired, so that it is possible to calibrate the components with a high degree of accuracy by performing rotation and multiplication operations on the spectra of the components in the unknown mixed sample in the multivariate space and lowering the correlation of each of the spectra of the components of the unknown mixed sample.

Meanwhile, in the embodiment, after the small dataset for calibration is determined, the Raman spectrum E1 of the unknown sample acquired under the same measurement conditions as that of the corresponding small dataset for calibration is determined as data for performing the calibration, but at that point in time, the Raman spectral data E1 of the unknown sample may be measured only under the above-mentioned measurement conditions, and the data may be selected from among the Raman spectral datasets E1, E2 and E3 of the unknown sample previously acquired under the different measurement conditions C1 to C3.

Next, the vibrational spectrum analysis method according to a third embodiment of the invention will be described below with reference to the drawings.

The vibrational spectrum analysis method according to the embodiment is a method of performing PCA calibration of the components of the unknown mixed sample to be analyzed.

Figure 5:
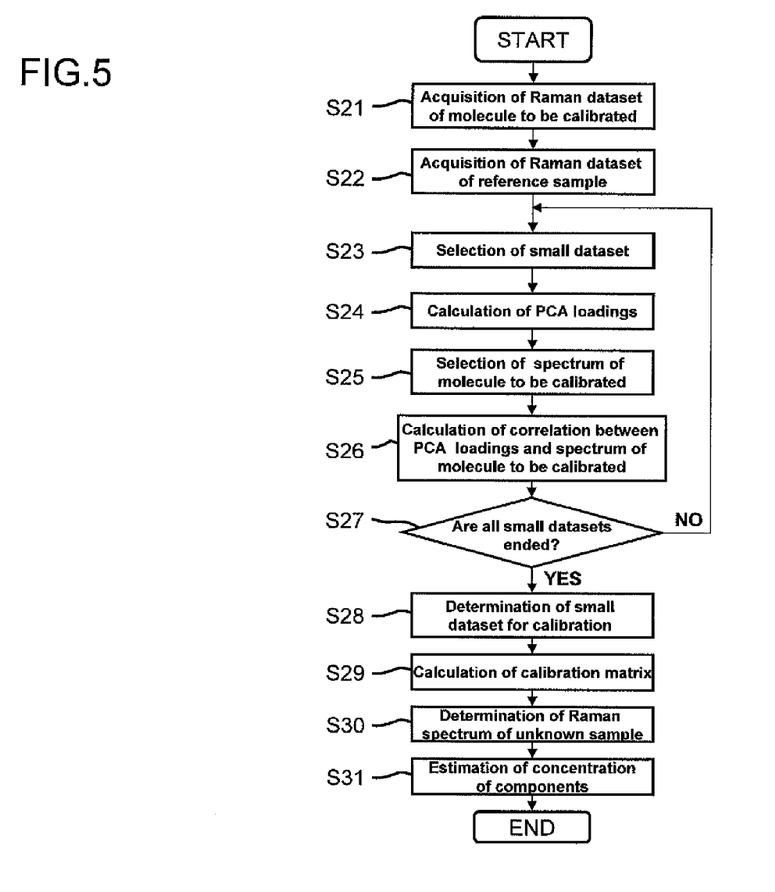
FIG. 5 is a flow diagram illustrating the vibrational spectrum analysis method according to a third embodiment of the invention.

In the vibrational spectrum analysis method according to the embodiment, a plurality of measurement conditions regarding the unknown mixed sample, the reference mixed sample and the molecule to be calibrated can be set, and as shown in FIG. 5, the Raman spectrum is first acquired by switching the measurement conditions in the molecule to be calibrated, to acquire the Raman spectral dataset of the molecule to be calibrated which includes Raman spectral data having different spectral profiles (step S21).

Here, the molecule to be calibrated is a molecule intended to be calibrated within the unknown mixed sample. For example, it is envisioned that the molecule to be calibrated is a specific protein molecule, or a specific saccharide molecule. As the molecule to be calibrated, one kind of molecule may be prepared, and two kinds of molecules may be prepared.

For example, a case will be described of acquiring the Raman spectral dataset of the molecule to be calibrated with respect to one kind of molecule to be calibrated.

Next, a Raman spectral dataset of a reference sample including a plurality of Raman spectral data items of the reference mixed sample for calculating the calibration matrix is acquired (step S22).

The Raman spectra having different spectral profiles are acquired with respect to the reference mixed sample by setting different measurement conditions for each of a plurality of reference mixed samples. When the Raman spectra of each of the reference mixed samples are acquired, the measurement is perform with respect to each of the reference mixed samples by setting a plurality of measurement conditions. A method of acquiring the Raman spectra having different spectral profiles by setting a plurality of measurement conditions is based on the method described in detail in the description of the above-mentioned first embodiment. Thereby, a plurality of Raman spectral data items is obtained which is acquired by setting different measurement conditions for each reference mixed sample. That is, the Raman spectral dataset of the reference sample is acquired which includes the Raman spectral data of a number corresponding to the number of the product of the number of the measurement conditions and the number of the reference mixed samples.

Next, any of the small datasets is selected from the Raman spectral dataset of the reference sample (step S23). The small dataset is indicative of a set of Raman spectral data acquired under the same measurement conditions in the Raman spectral dataset of the reference sample.

Next, the PCA loading is calculated using the selected small dataset (step S24).

The Raman spectral data measured under the same measurement conditions as those of the small dataset selected in step S13 are selected from the Raman spectral dataset of the molecule to be calibrated acquired in step S21 (step S25).

Thereafter, the correlation between the selected Raman spectral data of the molecule to be calibrated and the PCA loading of the small dataset calculated in step S24 is calculated (step S26). That is, when the correlation between the PCA loading which is a loading of the principle component included in the reference mixed sample and the Raman spectrum of the molecule to be calibrated is high, it is possible to select the principle component axis capable of satisfactorily grasping the concentration fluctuation of the molecule to be calibrated within the reference mixed sample.

Theses steps S23 to S26 are repeated (step S27), so that the correlations between the PCA loadings of the small dataset of the reference mixed sample of all the measurement conditions and the Raman spectra of the molecule to be calibrated are calculated, the calculated correlations are compared with each other to determine the small dataset having the PCA loading with a highest correlation as a small dataset for calibration (step S28), and the calibration matrix is calculated using the determined small dataset for calibration (step S29).

In addition, when the small dataset for calibration is determined, the Raman spectral data of the unknown sample are determined which are acquired by performing the measurement with the unknown mixed sample under the same measurement conditions as the measurement conditions at the time of acquiring the corresponding small dataset for calibration (step S30). The calibration of the components within the unknown mixed sample can be performed by multiplying the determined unknown sample Raman spectral data by the calculated calibration matrix (step S31).

According to the vibrational spectrum analysis method of the embodiment having such a configuration, since the Raman spectrum dataset having the highest correlation between the PCA loading calculated from the corresponding small dataset for calibration and the Raman spectrum of the molecule to be calibrated is selected as the small dataset for calibration for calculating the calibration matrix, there is an advantage that it is possible to calibrate the components with a high degree of accuracy by performing rotation and multiplication operations on the spectra of the components in the unknown mixed sample in the multivariate space and lowering the correlation of each of the spectra of the components of the unknown mixed sample.

Meanwhile, even in the embodiment, the Raman spectral dataset of the molecule to be calibrated is acquired, and then the Raman spectral dataset of the unknown mixed sample is acquired, but instead, the order may be reversed. In addition, the order of calculation step S24 of the PCA loading and selection step S25 of the spectrum of the molecule to be calibrated may be changed.

Next, the vibrational spectrum analysis method according to a fourth embodiment of the invention will be described below with reference to the drawings.

The vibrational spectrum analysis method according to the embodiment is a method of classifying a plurality of unknown mixed samples to be analyzed through the PCA in accordance with a desired benchmark molecule to be classified.

Figure 6:
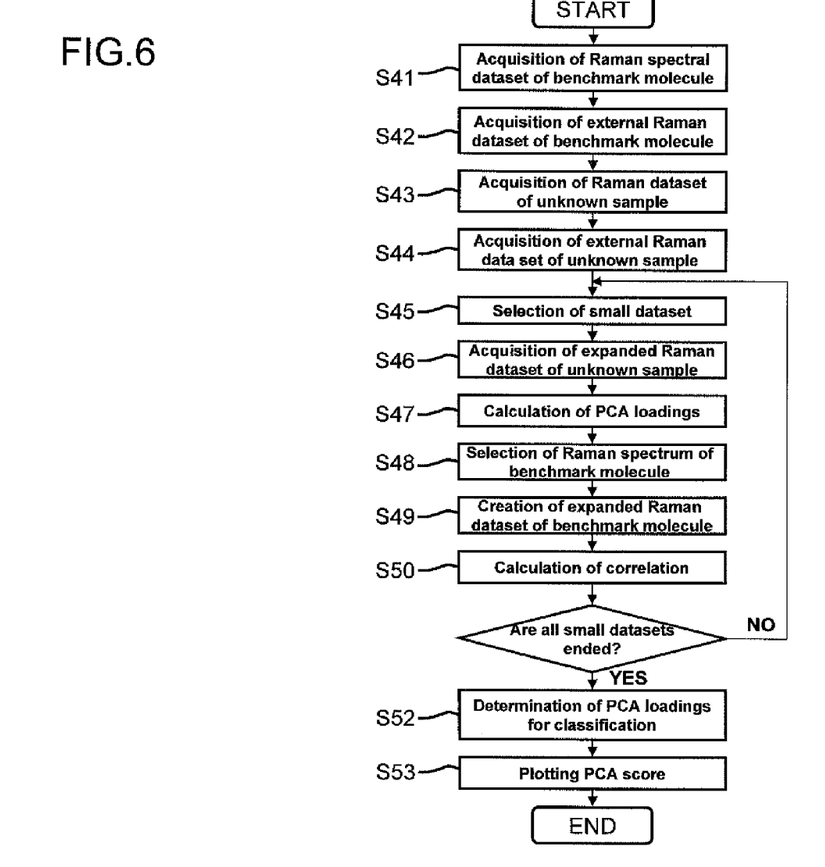
FIG. 6 is a flow diagram illustrating the vibrational spectrum analysis method according to a fourth embodiment of the invention.
Figure 7:
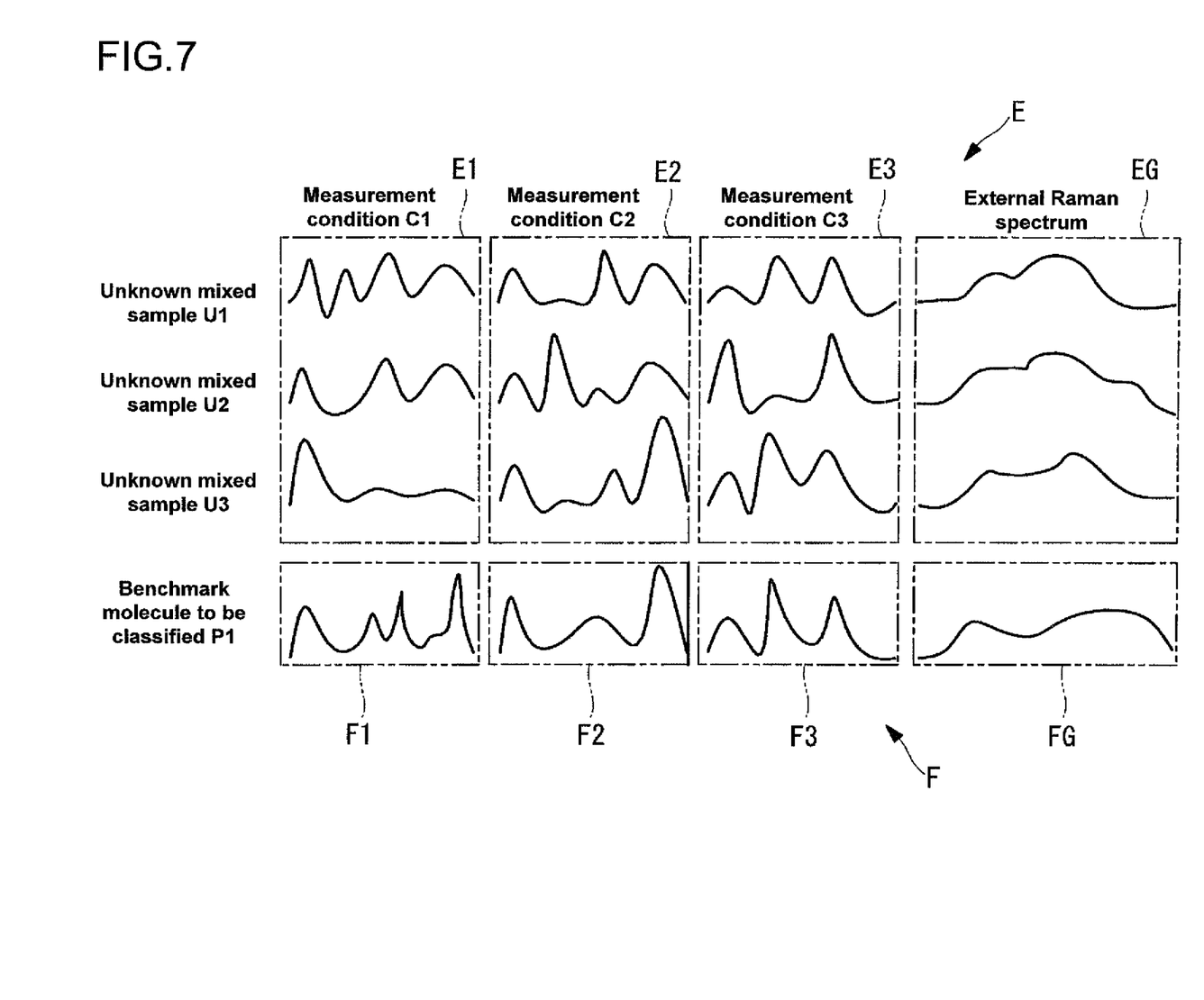
FIG. 7 is a diagram illustrating an example of a Raman spectral dataset of an unknown sample including Raman spectral data of a plurality of unknown mixed samples used in the vibrational spectrum analysis method of FIG. 6, benchmark molecule Raman spectral data of a benchmark molecule to be classified, and an external Raman spectrum thereof.
Figure 8:
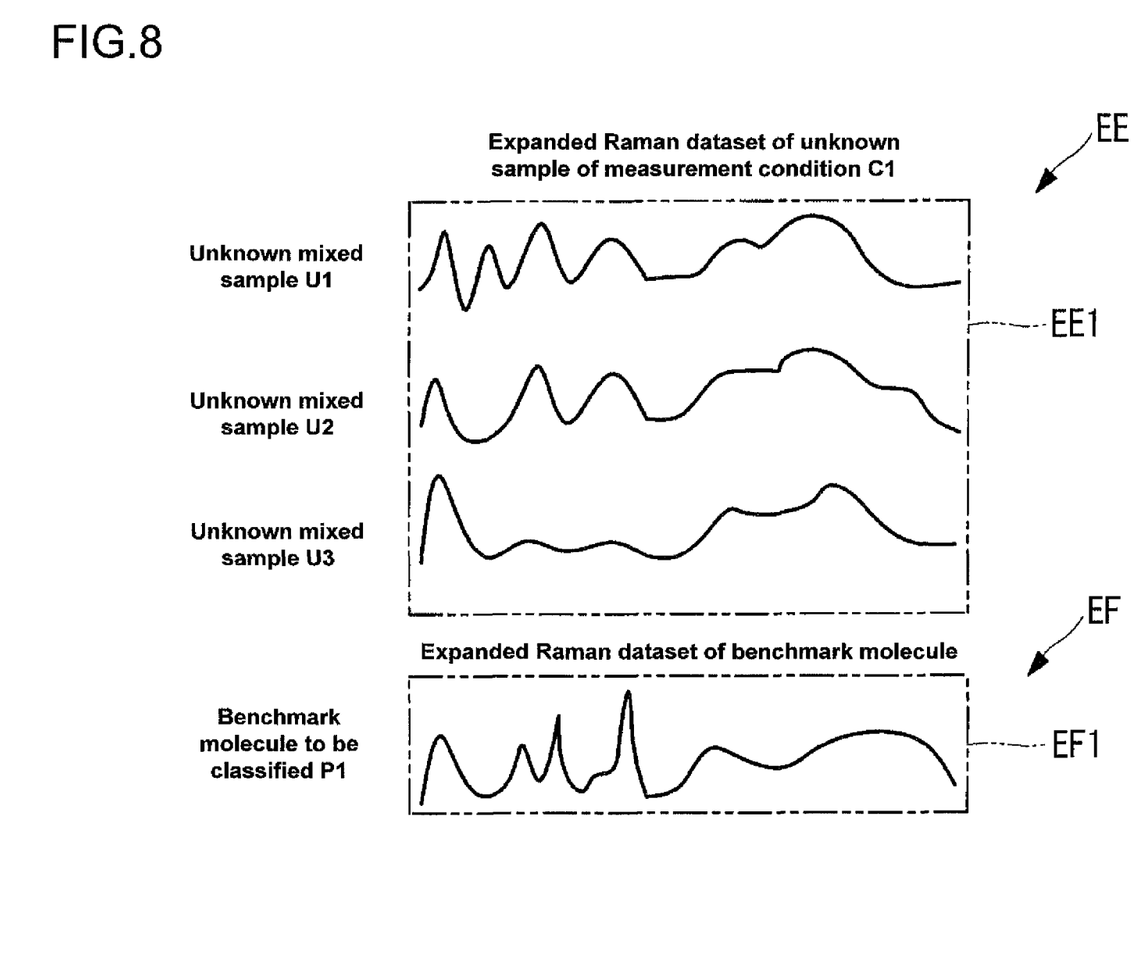
FIG. 8 is a diagram illustrating an example of an expanded Raman spectral dataset of an unknown sample in which the Raman spectral dataset of an unknown sample and the external Raman spectra of FIG. 7 are combined and an expanded Raman spectrum of a benchmark molecule in which the benchmark molecule Raman spectral data of a benchmark molecule to be classified and the external Raman spectra are combined.

In the vibrational spectrum analysis method according to the embodiment, the measurement conditions C1 to C3 regarding the unknown mixed sample and the benchmark molecule to be classified can be set, and as shown in FIGS. 6 to 8, the Raman spectrum is first acquired by switching the measurement conditions C1 to C3 in the benchmark molecule P1 to be classified, to acquire a Raman spectral dataset F of the benchmark molecule which includes the Raman spectral data F1 to F3 having different spectral profiles (step S41). A method of acquiring the Raman spectra having different spectral profiles by setting a plurality of measurement conditions is based on the method described in detail in the description of the above-mentioned first embodiment. In the benchmark molecule P1 to be classified, external Raman data FG which are Raman spectral data in a different frequency domain are acquired (step S42). In FIG. 7, a case is shown where the Raman spectral dataset F of the benchmark molecule and the external Raman data FG are acquired with respect to one kind of benchmark molecule P1 to be classified.

Next, the Raman spectral dataset E of the unknown sample including a plurality of Raman spectral data items E1 to E3 of the unknown mixed samples U1 to U3 is acquired (step S43).

As shown in FIG. 7, the Raman spectra having different spectral profiles are acquired with respect to the unknown mixed samples U1 to U3 by setting different measurement conditions C1 to C3 for each of a plurality of unknown mixed samples U1 to U3. At the time of acquisition of the above-mentioned Raman spectra, the measurement is performed with respect to each of the unknown mixed samples U1 to U3. Thereby, a plurality of Raman spectral data items acquired by setting different measurement conditions C1 to C3 is obtained for each of the unknown mixed samples U1 to U3. That is, the Raman spectral dataset E of the unknown sample is acquired which includes the Raman data of a number corresponding to the number of the product of the number of the measurement conditions and the number of the unknown mixed samples.

In addition, an external Raman spectral dataset EG is acquired which is Raman spectral data in a frequency domain different from that in which the Raman spectral dataset E of the unknown sample is acquired with respect to each of the unknown mixed samples U1 to U3 (step S44).

Next, any of the small datasets E1 to E3 is selected from the Raman spectral dataset E of the unknown sample (step S45). The small datasets E1 to E3 are indicative of a set of Raman spectral data acquired under the same measurement conditions in the Raman spectral dataset E of the unknown sample. For example, in the example shown in FIG. 7, the Raman spectral data having different spectral profiles are acquired by acquiring the Raman spectra, respectively, under three kinds of measurement conditions C1 to C3 with respect to each of the unknown mixed samples U1 to U3, and at first, the small dataset E1 including three Raman spectral data in a vertical column of the measurement conditions C1 is select from them.

Next, an expanded Raman spectral dataset EE1 of the unknown sample is created which includes a set of expanded Raman spectral data in which the selected Raman spectral data within the small dataset E1 and the Raman spectral data of the external Raman spectral dataset EG are combined for each of the unknown mixed samples U1 to U3 (step S46). The PCA loading is calculated using the created expanded Raman spectral dataset EE1 of the unknown sample (step S47).

On the other hand, the Raman spectral data F1 measured under the same measurement conditions C1 as those of the small dataset E1 selected in step S45 are selected from the Raman spectral dataset F of the benchmark molecule acquired in step S41 (step S48).

Expanded Raman spectral data EF1 of the benchmark molecule are created in which the selected Raman spectral data F1 of the benchmark molecule P1 to be classified and the external Raman data FG acquired in step S42 with respect to the benchmark molecule P1 to be classified are combined (step S49).

After this, the correlation between the PCA loading calculated in step S46 and the expanded Raman spectral data EF1 of the benchmark molecule is calculated (step S50).

These steps S45 to S49 are repeated similarly with respect to the small datasets E2 and E3 (step S51), so that the correlation between the PCA loading of an expanded Raman spectral dataset EE of the unknown sample of the unknown mixed samples U1 to U3 of all the measurement conditions C1 to C3 and an expanded Raman spectral data FE of the benchmark molecule is calculated, and the calculated correlations are compared with each other to determine the PCA loading having the highest correlation as a PCA loading for classification (step S52). Using the determined PCA loading for classification, the PCA score is plotted for each of the unknown mixed samples U1 to U3 (step S53). Thereby, the unknown mixed samples U1 to U3 are classified with respect to the benchmark molecule P1 to be classified.

As described above, according to the vibrational spectrum analysis method of the embodiment, since the expanded Raman spectral dataset EE of the unknown sample is used with which the external Raman spectral data EG acquired in a different frequency domain for each of the unknown mixed samples U1 to U3 is combined, it is possible to raise the number of dimensions of the space in the multivariate space in which a spectrum group of the unknown mixed sample is represented as a point group on the space, and to further generate the dispersion in the point group distribution of the spectrum of the unknown mixed sample. In this way, there is an advantage that it is possible to further perform rotation and multiplication operations on the spectrum of the unknown mixed sample, and to classify the unknown mixed samples U1 to U3 with a high degree of accuracy with respect to the benchmark molecule P1 to be classified on the basis of the PCA loading capable of most satisfactorily grasping the concentration fluctuation of the benchmark molecule P1 to be classified.

Meanwhile, even in the embodiment, the Raman spectral dataset of the benchmark molecule P1 to be classified is acquired, and then the Raman spectral dataset of the unknown mixed samples U1 to U3 is acquired, but instead, the order may be reversed. In addition, the orders of steps S46 and S47 and steps S48 and S49 may be changed.

REFERENCE SIGNS LIST

P1: BENCHMARK MOLECULE TO BE CLASSIFIED
R1, R2 and R3: REFERENCE MIXED SAMPLE
S3, S14, S24 and S47: CALCULATION STEP
S4, S16, S26, and S50: CORRELATION CALCULATION STEP
S6, S18, S28 and S52: DETERMINATION STEP
S7 and S29: CALIBRATION MATRIX CALCULATION STEP
S8, S30 and S45: UNKNOWN SAMPLE DATASET SELECTION STEP
S9 and S31: CALIBRATION STEP
S13: DATASET SELECTION STEP
S15 and S25: SPECTRUM SELECTION STEP
S19 and S53: PLOTTING STEP
S46: UNKNOWN SAMPLE DATA COMBINATION STEP
S48: BENCHMARK MOLECULE SPECTRUM SELECTION STEP
S49: BENCHMARK MOLECULE DATA COMBINATION STEP
U1, U2 and U3: UNKNOWN MIXED SAMPLE

The invention claimed is:
1. A computer-implemented method of vibrational spectrum analysis of an unknown mixed sample, the computer comprising a processor, the method comprising steps of:

a first measuring step of measuring, by a measuring apparatus controlled by the computer, under a first measurement condition a first Raman spectrum of a benchmark molecule, the measuring apparatus at least having a light source and a Raman spectrum detector;

a second measuring step of measuring, by the measuring apparatus controlled by the computer, under a second measurement condition, different from the first measurement condition, a second Raman spectrum of the benchmark molecule, wherein the first measurement condition differs from the second measurement condition with respect to at least one of: (a) a different light irradiation condition and (b) a different detection condition and wherein a measurement obtained in the first measurement step and a measurement obtained in the second measurement step are stored in a storage of the computer;

a dataset selection step of selecting, by the processor, a plurality of small datasets of a Raman spectral dataset, each small dataset including Raman spectral data of a plurality of unknown mixed samples acquired under the same measurement condition in reference to the measurements stored in the storage of the computer, selected from the first measurement condition and the second measurement condition, wherein the Raman spectral dataset includes a plurality of Raman spectral data items having different spectral profiles acquired based on physical properties of the samples including at least one of a degree of depolarization and a vibrational phase relaxation time with respect to the plurality of unknown mixed samples including a plurality of unknown components at an unknown mixture ratio;

a calculation step of calculating, by the processor, PCA loadings from the small datasets selected in the dataset selection step, the PCA loadings being loadings of principal component analysis;

a spectrum selection step of selecting, by the processor, a respective Raman spectrum that is preliminarily acquired under the same measurement condition as those of each small dataset selected in the dataset selection step, in the Raman spectra of the benchmark molecule to be classified which is a component intended to be classified;

a correlation calculation step of calculating, by the processor, a correlation between the PCA loadings calculated in the calculation step and each Raman spectrum of the benchmark molecule to be classified selected in the spectrum selection step;

a determination step of determining, by the processor, a PCA loading which has the highest correlation with the Raman spectrum of the benchmark molecule to be classified, in the PCA loadings calculated from the plurality of small datasets having different measurement conditions; and a classification step of classifying, by the processor, the unknown mixed samples with respect to the benchmark molecule to be classified by plotting a PCA score with respect to the PCA loading determined in the determination step.

* * * * *